(12) United States Patent
Millet

(10) Patent No.: US 10,973,786 B2
(45) Date of Patent: Apr. 13, 2021

(54) R-BETA-HYDROXYBUTYRATE, S-BETA-HYDROXYBUTYRATE, AND RS-BETA-HYDROXYBUTYRATE MIXED SALT COMPOSITIONS

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

(21) Appl. No.: 16/996,509

(22) Filed: Aug. 18, 2020

(65) Prior Publication Data

US 2020/0375927 A1 Dec. 3, 2020

Related U.S. Application Data

(60) Continuation-in-part of application No. 16/783,886, filed on Feb. 6, 2020, and a continuation-in-part of application No. 16/783,956, filed on Feb. 6, 2020, and a continuation-in-part of application No. 16/783,844, filed on Feb. 6, 2020, and a continuation-in-part of application No. 16/720,211, filed on Dec. 19, 2019, said application No. 16/783,844 is a continuation-in-part of application No. 16/409,501, filed on May 10, 2019, now Pat. No. 10,596,131, said application No. 16/720,211 is a division of application No. 16/272,145, filed on Feb. 11, 2019, now Pat. No. 10,736,861, said application No. 16/783,886 is a continuation-in-part of application No. 16/272,192, filed on Feb. 11, 2019, now Pat. No. 10,596,130, said application No. 16/409,501 is a continuation-in-part of application No. 16/272,165, filed on Feb. 11, 2019, now Pat. No. 10,596,129, which is a continuation of application No. 16/224,408, filed on Dec. 18, 2018, now Pat. No. 10,588,876, said application No. 16/272,192 is a continuation-in-part of application No. 16/224,485, filed on Dec. 18, 2018, now Pat. No. 10,596,128, which is a division of application No. 15/936,849, filed on Mar. 27, 2018, now Pat. No. 10,245,243, said application No. 16/224,408 is a continuation-in-part (Continued)

(51) Int. Cl.
| | |
|---|---|
| *A61K 31/19* | (2006.01) |
| *A61K 47/14* | (2017.01) |
| *A61K 9/14* | (2006.01) |
| *A61K 9/20* | (2006.01) |
| *A61K 9/48* | (2006.01) |
| *A61P 3/08* | (2006.01) |
| *A23L 29/00* | (2016.01) |
| *A23L 33/12* | (2016.01) |
| *A23L 33/00* | (2016.01) |
| *A23L 33/10* | (2016.01) |
| *A23L 33/155* | (2016.01) |

(52) U.S. Cl.
CPC ............ *A61K 31/19* (2013.01); *A23L 29/035* (2016.08); *A23L 33/10* (2016.08); *A23L 33/12* (2016.08); *A23L 33/30* (2016.08); *A61K 9/14* (2013.01); *A61K 9/20* (2013.01); *A61K 9/48* (2013.01); *A61K 47/14* (2013.01); *A61P 3/08* (2018.01); *A23L 33/155* (2016.08); *A23V 2002/00* (2013.01); *A23V 2250/182* (2013.01); *A23V 2250/192* (2013.01); *A23V 2250/1946* (2013.01); *A23V 2250/7106* (2013.01)

(58) Field of Classification Search
CPC .... A61K 31/19; A61K 9/0053; A61K 31/047; A61K 47/14; A61K 9/14; A61K 9/48
See application file for complete search history.

(56) References Cited

U.S. PATENT DOCUMENTS

| | | |
|---|---|---|
| 2,238,149 A | 4/1941 | Aeckerle |
| 2,976,073 A | 3/1961 | Russell et al. |
| (Continued) | | |

FOREIGN PATENT DOCUMENTS

| | | |
|---|---|---|
| CN | 1347319 A | 5/2002 |
| EP | 2283834 A2 | 2/2011 |
| (Continued) | | |

OTHER PUBLICATIONS

Dietary Guidelines Recommendations at https://health.gov/our-work/food-nutrition/2015-2020-dietary-guidelines/guidelines/appendix-7/ (2010) (retrieved from the internet Oct. 20, 2020) (Year: 2010).*
Vandenberghe et al. in Can. J. Physiol. Pharmacol. 95: 455-458 (2017) (Published at www.nrcresearchpress .com/cjpp on Nov. 25, 2016). (Year: 2016).*
A New Toy Measuring Blood Ketones. Diet Doctor, Aug. 21, 2012. Dowloaded Apr. 1, 2015. http://www.dietdoctor.com/a-new-toy-measuring-blood-ketoones.
Arendash et al. "Caffeine and Coffee as Therapeutics Against Alzheimer's Disease", Journal of Alzheimer's Disease 20, 2010, S117-S126.

(Continued)

*Primary Examiner* — Dennis Heyer
(74) *Attorney, Agent, or Firm* — Workman Nydegger

(57) ABSTRACT

Beta-hydroxybutyrate (BHB) mixed salts are formulated to induce or sustain ketosis in a subject. The BHB mixed salts provide a biologically balanced set of cationic electrolytes and avoid detrimental health effects associated with imbalanced electrolyte ratios. BHB mixed salt compositions include two, three or four of sodium BHB, potassium BHB, calcium BHB, or magnesium BHB. BHB mixed salt compositions include R-BHB and/or S-BHB, such as enriched with either R-BHB or S-BHB. BHB mixed salt compositions may include BHB mixed salts and beta-hydroxybutyric acid. BHB mixed salts may be provided as or mixed with a dietetically or pharmaceutically acceptable carrier. BHB mixed salt compositions can be a solid, such as a powder, or a liquid, such as a beverage. A mixed salt-acid composition is particularly well-suited for flavored beverages.

24 Claims, No Drawings

Related U.S. Application Data of application No. 15/936,820, filed on Mar. 27, 2018, now Pat. No. 10,245,242, said application No. 16/272,145 is a continuation-in-part of application No. 15/454,157, filed on Mar. 9, 2017, now Pat. No. 10,292,952.

(60) Provisional application No. 62/805,054, filed on Feb. 13, 2019, provisional application No. 62/607,578, filed on Dec. 19, 2017, provisional application No. 62/590,063, filed on Nov. 22, 2017, provisional application No. 62/307,203, filed on Mar. 11, 2016.

(56) References Cited

U.S. PATENT DOCUMENTS

| | | | |
|---|---|---|---|
| 5,093,044 A | 3/1992 | Wretlind et al. | |
| 5,116,868 A | 5/1992 | Chen et al. | |
| 5,654,266 A | 8/1997 | Chen et al. | |
| 5,700,670 A | 12/1997 | Yamagishi et al. | |
| 6,207,856 B1 | 3/2001 | Veech | |
| 6,316,038 B1 | 11/2001 | Veech | |
| 6,323,237 B1 | 11/2001 | Veech | |
| 6,380,244 B2 | 4/2002 | Martin et al. | |
| 6,613,356 B1 | 9/2003 | Vlahakos | |
| 6,706,756 B1 | 3/2004 | Fitzpatrick et al. | |
| 6,835,750 B1 | 12/2004 | Henderson | |
| 7,351,736 B2 | 4/2008 | Veech | |
| 7,807,718 B2 | 10/2010 | Hashim et al. | |
| 8,101,653 B2 | 1/2012 | Veech | |
| 8,124,589 B2 | 2/2012 | Henderson | |
| 8,426,468 B2 | 4/2013 | Henderson | |
| 8,642,654 B2 | 2/2014 | Clarke et al. | |
| 8,748,400 B2 | 6/2014 | Henderson | |
| 9,138,420 B2 | 9/2015 | D'Agostino et al. | |
| 9,211,275 B2 | 12/2015 | Clarke et al. | |
| 9,675,577 B2 | 6/2017 | D'Agostino et al. | |
| 9,717,767 B2 | 8/2017 | Carpenter et al. | |
| 9,795,580 B2 | 10/2017 | Weeber et al. | |
| 9,808,481 B2 | 11/2017 | Ritter et al. | |
| 9,957,246 B2 | 5/2018 | Stinchcomb et al. | |
| 10,022,409 B2 | 7/2018 | Carpenter et al. | |
| 10,051,880 B2 | 8/2018 | Clarke et al. | |
| 10,245,242 B1 | 4/2019 | Millet | |
| 10,245,243 B1 | 4/2019 | Millet | |
| 10,292,592 B2 | 5/2019 | Marshall et al. | |
| 10,292,952 B2 | 5/2019 | Millet | |
| 10,588,877 B2 | 3/2020 | Arnold | |
| 10,660,958 B2 | 5/2020 | Clarke | |
| 2001/0014696 A1 | 8/2001 | Veech | |
| 2001/0041736 A1 | 11/2001 | Veech | |
| 2002/0013339 A1 | 1/2002 | Martin et al. | |
| 2003/0022937 A1 | 1/2003 | Veech | |
| 2004/0266872 A1 | 12/2004 | Veech | |
| 2005/0129783 A1 | 6/2005 | McCleary et al. | |
| 2007/0179197 A1 | 8/2007 | Henderson | |
| 2008/0058416 A1 | 3/2008 | Greenwood et al. | |
| 2008/0287372 A1 | 11/2008 | Henderson | |
| 2009/0253781 A1 | 10/2009 | Veech | |
| 2010/0041751 A1 | 2/2010 | Henderson | |
| 2010/0197758 A1 | 8/2010 | Andrews et al. | |
| 2010/0298294 A1 | 11/2010 | Clarke et al. | |
| 2012/0071548 A1 | 3/2012 | Veech | |
| 2013/0079406 A1 | 3/2013 | Veech | |
| 2015/0065571 A1 | 3/2015 | Clarke et al. | |
| 2015/0132280 A1 | 5/2015 | Lopez et al. | |
| 2016/0193173 A1 | 7/2016 | Clarke et al. | |
| 2016/0256411 A1 | 9/2016 | Aung-Din | |
| 2017/0020844 A1 | 1/2017 | Galinski | |
| 2017/0172969 A1 | 6/2017 | D'Agostino et al. | |
| 2017/0258745 A1 | 9/2017 | Millet | |
| 2017/0266148 A1 | 9/2017 | D'Agostino et al. | |
| 2017/0290792 A1* | 10/2017 | Cavaleri | A61K 36/82 |
| 2017/0296501 A1 | 10/2017 | Lowery et al. | |
| 2017/0298339 A1 | 10/2017 | Hanson et al. | |
| 2017/0304564 A1 | 10/2017 | Dehaan et al. | |
| 2018/0021274 A1* | 1/2018 | Arnold | A61K 9/48 514/557 |
| 2018/0055797 A1 | 3/2018 | Llosa et al. | |
| 2018/0057846 A1 | 3/2018 | Llosa et al. | |
| 2018/0195096 A1 | 7/2018 | Veech et al. | |
| 2019/0099394 A1 | 4/2019 | Ari et al. | |
| 2019/0167613 A1 | 6/2019 | Millet | |
| 2019/0313682 A1 | 10/2019 | Nagel | |

FOREIGN PATENT DOCUMENTS

| | | | |
|---|---|---|---|
| EP | 2976073 A1 | 1/2016 | |
| EP | 3094321 A1 | 11/2016 | |
| JP | 11-060434 A | 3/1999 | |
| JP | 2002-521330 A | 7/2002 | |
| RU | 2345546 C2 | 2/2009 | |
| WO | 87/03808 A1 | 7/1987 | |
| WO | 98/41200 A1 | 9/1998 | |
| WO | 03/70823 A2 | 8/2003 | |
| WO | 2005/107724 A1 | 11/2005 | |
| WO | 2007/115282 A2 | 10/2007 | |
| WO | 2008/005818 A1 | 1/2008 | |
| WO | 2008/021394 A2 | 2/2008 | |
| WO | 2008/024408 A2 | 2/2008 | |
| WO | 2011/101171 A1 | 8/2011 | |
| WO | 2013/150153 A1 | 10/2013 | |
| WO | 2014/153416 A1 | 9/2014 | |
| WO | 2015/071811 A1 | 5/2015 | |
| WO | 2015/156865 A1 | 10/2015 | |
| WO | 2016/123229 A1 | 8/2016 | |
| WO | 2017/208217 A2 | 12/2017 | |
| WO | 2018/089863 A1 | 5/2018 | |
| WO | 2019/018683 A1 | 1/2019 | |
| WO | 2019/237152 A1 | 12/2019 | |

OTHER PUBLICATIONS

Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).

Bastin et al., "Salt Slection and Optimisation Procedures for Pharmaceutical New Chemical Entities", American Chemical Society and The Royal Society of Chemistry, vol. 4, No. 5, 2000, pp. 427-435.

Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.

Dolson, Laura. How to Test Your Blood for Ketones. Downloaded Apr. 1, 2015. htpp://lowcarbdiets.about.com/od/KetogenicDiets/a/How-to-Test-Blodd-For-Ketones.htm.

First Examination Report for New Zealand Patent Application No. 711433 issued by the New Zealand Intellectual Property Office dated Mar. 10, 2016.

First Office Action issued by the Chinese State Intellectual Property Office dated Nov. 4, 2016 for corresponding Chinese Patent Application No. 201480016818.0.

Hashim, Sarni A., et al., "Ketone body therapy: from the ketogenic diet to the oral administration of ketone ester", Journal of Lipid Research, vol. 55, 2014.

Haywood A, Glass BD. Pharmaceutical excipient—where do we begin? Australian Prescriber. 2011; 34: 112-114.

Henderson, Samuel T. "Ketone Bodies as a Therapeutic for Alzheimer's Disease." Neurotherapeutics. Jul. 2008;5(3):470-80.

International Search Report and Written Opinion issued in PCT/US19/48357 dated Nov. 18, 2019.

International Search Report and Written Opinion issued in PCT/US19/48364 dated Nov. 15, 2019.

International Search Report and Written Opinion issued in PCT/US20/17552 dated May 4, 2020.

International Search Report and Written Opinion issued in PCT/US20/17555 dated May 4, 2020.

International Search Report and Written Opinion issued in PCT/US20/17556 dated May 4, 2020.

(56) References Cited

OTHER PUBLICATIONS

International Search Report and Written Opinion received for PCT Patent Application No. PCT/US2020/033159, dated Aug. 12, 2020, 9 pages.
International Search Report cited in PCT/US18/62093 dated Feb. 1, 2019.
International Search Report cited in PCT/US18/62096 dated Feb. 11, 2019.
International Search Report cited in PCT/US19/27214 dated Jun. 25, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
Karppanen, H., et al, "Why and how to implement sodium, potassium, calcium, and magnesium changes in food items and diets?"
Kesl, et al., "Effects of exogenous ketone supplementation on blood ketone, glucose, triglyceride, and lipoprotein levels in Sprague-Dawley rats", Nutrition & Metabolism (2016).
Kirsch, Jr et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, M. "Value of VLCD Supplementation with Medium Chain Triglycerides." I'nt J Obes Relat Metab Disord. Sep. 2001;25(9):1393/\00.
Murray, Andrew J., et al. "Novel ketone diet enhances physical and cognitive performance", The FASEB Journal, Vo. 30 Dec. 2016.
Nova Max Plus Glucose and Ketone Testing with One Monitor. Downloaded Apr. 1, 2015. http://www.novacares.com/nova-max-plus/.
Parker, Steve, "Ketogenic Mediterranean Diet: Version 2.3," Nov. 23, 2010, pp. 1-3. (Year: 2010).
PCT International Search Report and Written Opinion cited in PCT/US2014/031237 dated Jul. 15, 2014.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nlm.nih.gov/compound/Acetoacetic-acid, Retrieved on Sep. 3, 2019.
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. in Journal of Liquid Chromatography & Related Technologies, 33:1047-1057 (2010) (Year: 2010).

Serum Ketones Test. MedlinePlus Medical Encyclopedia. Downloaded Apr. 1, 2015. http://www.nlm.nih.gov/medlineplus/ency/article/003498.htm.
Shigeno etal. in Biosci. Biotech. Biochem., 56(2), 320-323 (1992) (Year: 1992).
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Notice of Allowance received for U.S. Appl. No. 16/381,202, dated Nov. 10, 2020, 8 pages.
Requirement for Restriction/Election received for U.S. Appl. No. 16/551,570, dated Sep. 28, 2020, 6 pages.
Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Holtzman et al., "Role of adenosine receptors in caffeine tolerance", J. Pharmacol. Exp. Ther., 1991 ;256(1 ):62-68.
International Search Report and Written Opinion received for PCT Patent Application No. PCT/US20/37289, dated Sep. 30, 2020, 8 pages.
Non-Final Rejection dated Sep. 9, 2020 for U.S. Appl. No. 16/783,956.
Office Action cited in U.S. Appl. No. 16/720,211 dated Oct. 28, 2020.
Parker, Steve, "Ketogenic Mediterraanean Diet: Version 2.3," Nov. 23, 2010, pp. 1-3. (Year: 2010).

\* cited by examiner

R-BETA-HYDROXYBUTYRATE, S-BETA-HYDROXYBUTYRATE, AND RS-BETA-HYDROXYBUTYRATE MIXED SALT COMPOSITIONS

CROSS-REFERENCE TO RELATED APPLICATIONS

This Application is a CIP of U.S. application Ser. No. 16/783,844, filed Feb. 6, 2020, which is a CIP of U.S. application Ser. No. 16/409,501, filed May 10, 2019, now U.S. Pat. No. 10,596,131, which is a CIP of U.S. application Ser. No. 16/272,165, filed Feb. 11, 2019, now U.S. Pat. No. 10,596,129, which is a CIP of U.S. application Ser. No. 16/224,408, filed Dec. 18, 2018, now U.S. Pat. No. 10,588,876, which is a DIV of U.S. application Ser. No. 15/936,820, filed Mar. 27, 2018, now U.S. Pat. No. 10,245,242, which claims the benefit of U.S. Prov App No. 62/590,063, filed Nov. 22, 2017.

This Application is also a CIP of U.S. application Ser. No. 16/783,886, filed Feb. 6, 2020, which is a CIP of U.S. application Ser. No. 16/272,192, filed Feb. 11, 2019, now U.S. Pat. No. 10,596,130, which is a CIP of U.S. application Ser. No. 16/224,485, filed Dec. 18, 2018, now U.S. Pat. No. 10,596,128, which is a DIV of U.S. application Ser. No. 15/936,849, filed Mar. 27, 2018, now U.S. Pat. No. 10,245,243, which claims the benefit of U.S. Prov App No. 62/607,578, filed Dec. 19, 2017.

This Application is also a CIP of U.S. application Ser. No. 16/783,956, filed Feb. 6, 2020, which claims the benefit of U.S. Prov App No. 62/805,054, filed Feb. 13, 2019.

This Application is also a CIP of U.S. application Ser. No. 16/720,211, filed Dec. 19, 2019, which is a DIV of U.S. application Ser. No. 16/272,145, filed Feb. 11, 2019, now U.S. Pat. No. 10,736,861, which is a CIP of U.S. application Ser. No. 15/454,157, filed Mar. 9, 2017, now U.S. Pat. No. 10,292,952, which claims the benefit of U.S. Prov App No. 62/307,203, filed Mar. 11, 2016.

The foregoing patents and applications are incorporated by reference in their entirety.

BACKGROUND

1. Field of the Invention

The invention relates to R-beta-hydroxybutyrate, S-beta-hydroxybutyrate, and RS-beta-hydroxybutyrate mixed salt compositions and methods for producing elevated blood levels of ketone bodies in a subject.

2. Related Technology

In periods of fasting, extreme exercise, and/or low carbohydrate consumption, glucose and glycogen stores in the body are rapidly used and can become depleted. Failure to replenish depleted glucose stores causes the body to metabolically shift to creation and use of ketone bodies for energy. Ketone bodies can be used by cells of the body as a fuel to satisfy the its energy needs, including the brain and heart. During prolonged fasting, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is known as "ketosis". At blood levels between 1.0 mmol/L and 3.0 mmol/L the condition is "nutritional ketosis."

Upon transitioning into ketosis, i.e., during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

During ketosis, the body is in ketogenesis and essentially burning fat for its primary fuel. The body cleaves fats into fatty acids and glycerol and transforms fatty acids into acetyl CoA molecules, which are then transformed through ketogenesis into the water-soluble ketone bodies beta-hydroxybutyrate (i.e., "β-hydroxybutyrate" or "BHB"), acetoacetate (also known as acetylacetonate), and acetone in the liver. Beta-hydroxybutyrate and acetoacetate are the primary ketone bodies used by the body for energy while acetone is removed and expelled as a by-product.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these is difficulty in transitioning to a ketogenic state. The fastest endogenous way to enter ketosis is by depleting glucose stores in the body through fasting and/or exercise. This is physically and emotionally demanding and extremely challenging for even the most motivated and disciplined.

Additionally, the transition into ketosis is accompanied by hypoglycemia, which causes lethargy, light-headedness, and an uncomfortable physiological and mental state commonly referred to as "low-carb flu." Some people may also experience a down regulation in metabolism as the body naturally goes into an "energy-saving" mode. Some suggest that these transition symptoms may last as long as two to three weeks. During this transition period, if a subject consumes a meal or snack containing carbohydrates above a restricted amount, ketogenesis immediately terminates, exiting the body from its state of ketosis as it shifts back to using glucose as its primary fuel, and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. This is further complicated by disruption of normal electrolyte balance, which often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis affects the rate at which certain electrolytes are extracted by the kidneys, additionally lowering electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

SUMMARY

Disclosed herein are ketogenic mixed salt compositions and methods for increasing ketone body level in a subject, including promoting and/or sustaining ketosis in a subject while promoting or maintaining a beneficial electrolytic balance.

In a first embodiment, mixed salt compositions include enantiomerically pure R-beta-hydroxybutyrate salts or a non-racemic mixture of R-beta-hydroxybutyrate and S-beta-hydroxybutyrate salts enriched with R-beta-hydroxybutyrate salts relative to S-beta-hydroxybutyrate salts.

In a second embodiment, mixed salt compositions include enantiomerically pure S-beta-hydroxybutyrate salts or a non-racemic mixture of S-beta-hydroxybutyrate salts and R-beta-hydroxybutyrate salts enriched with S-beta-hydroxybutyrate salts relative to R-beta-hydroxybutyrate salts.

In a third embodiment, example mixed salt compositions include a racemic mixture of R- and S-beta-hydroxybutyrate salts (i.e., a mixture having a 1:1 molar ratio of R-beta-hydroxybutyrate salts and S-beta-hydroxybutyrate salts.

In a fourth embodiment, the mixed salt compositions may include salts of acetoacetate, which is not a chiral molecule but is a readily metabolized ketone body that can be used in combination with or in place of beta-hydroxybutyrate salts.

In some embodiments, the mixed salt composition may be combined with a nutritionally or pharmaceutically acceptable carrier.

R-beta-hydroxybutyrate is the endogenous form of BHB produced by mammals and provides a greater and/or faster ketogenic effect compared to either a racemic mixture (RS-beta-hydroxybutyrate) or a BHB salt mixture enriched with or containing solely S-beta-hydroxybutyrate. Because the R-beta-hydroxybutyrate enantiomer is endogenously produced by a mammal during ketosis, administering the R-beta-hydroxybutyrate enantiomer to a subject provides an additional quantity and/or increased blood plasma level that can be immediately utilized by the body, such as for producing energy (e.g., as an alternative energy source to glucose).

S-beta-hydroxybutyrate, which is not endogenously produced by mammals and is believed to be unnatural and potentially harmful, can provide other beneficial effects. These include one or more of: increased endogenous production of R-beta-hydroxybutyrate and acetoacetate; endogenous conversion into one or both of R-beta-hydroxybutyrate and acetoacetate; endogenous conversion into fatty acids and sterols; prolonged ketosis; metabolism of S-beta-hydroxybutyrate independent of its conversion to R-beta-hydroxybutyrate and/or acetoacetate; improved fetal development; increased growth years; reduced endogenous production of acetone during ketosis; signaling to modulate metabolism of R-beta-hydroxybutyrate and glucose; antioxidant activity; and production of acetyl-CoA.

The mixed salt compositions described herein may function to induce and/or sustain ketosis in the subject to which the composition is administered without delivering too much total electrolyte to the body, or too much of a particular electrolyte that may be unhealthy, such as sodium and/or calcium (i.e., so as to not exceed the RDA for a particular electrolyte or only exceed it by a predetermined amount). This allows the mixed salt compositions to induce or sustain ketosis while simultaneously limiting, preventing, or improving electrolyte imbalance in the subject.

Mixed salts can be formed from a plurality of cations, e.g., at least three different cations, including cations selected from lithium, sodium, potassium, calcium, magnesium, transition metals, amines, and amino acids, and at least one anion selected from beta-hydroxybutyrate and acetoacetate. In some embodiments, mixed salt compositions are formulated from at least three different cations and a single anion, wherein the single anion is beta-hydroxybutyrate, and wherein other anions are omitted.

In embodiments, a mixed salt composition includes potassium BHB salt and sodium BHB salt in an amount, by weight, that is no greater than the amount, by weight, of the potassium BHB salt. In embodiments, a mixed salt composition includes magnesium BHB salt and calcium BHB salt in an amount, by weight, that is no greater than the amount, by weight, of the magnesium BHB salt.

By limiting the total quantity of sodium and/or calcium BHB salts or any other total quantity of single cationic electrolytes in the mixed salt composition (e.g., by including higher amounts of potassium BHB, magnesium BHB, one or more transition metal BHB salts, and/or one or more BHB-amino acid salts), it is possible to substantially increase the total quantity of BHB delivered to the body without delivering an excessive or unhealthy quantity of cationic electrolytes to the body.

Mixed salt ketogenic compositions can be useful as weight loss supplement, as treatment for high blood glucose or type II diabetes, as brain tonic, as athletic performance enhancer, as preventative against metabolic dysfunction, mitochondrial defect, insulin resistance, as adjunct to a ketogenic diet, as anti-aging supplement, and for other uses associated with improved metabolic health.

In some embodiments, the mixed salt composition is provided as a solid or powder form. Such solid-form ketogenic compositions, in addition to providing beneficial ketogenic effects and electrolyte balance, are formulated to provide for ease of handling and manufacturability. Alternatively, the composition may be in the form of a liquid mouth spray or drink for fast delivery and uptake.

The mixed salt compositions can include the free acid forms of beta-hydroxybutyrate. For example, mixed salt compositions may contain a plurality of beta-hydroxybutyrate salts in combination with R- and/or S-beta-hydroxybutyric acid. Including beta-hydroxybutyric acid with the beta-hydroxybutyrate salts beneficially reduces electrolyte load, increases absorption rate, improves taste, facilitates easier formulation, and reduces the need to add citric acid or other edible acids to obtain a composition having neutral or acidic pH.

Mixed salt compositions can be used in a method for increasing ketone body level in a subject in need thereof, including promoting and/or sustaining ketosis in the subject, comprising administering to the subject a nutritionally or pharmaceutically effective amount of a mixed salt composition disclosed herein. Benefits of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Introduction

Disclosed herein are ketogenic mixed salt compositions and methods for increasing ketone body level in a subject, including promoting and/or sustaining ketosis in a subject while promoting or maintaining a beneficial electrolytic balance.

As used herein, a "ketogenic composition" and "ketogenic mixed salt" are formulated to increase ketone body level in a subject, including inducing and/or sustaining a state of elevated ketone bodies at a desired level, such as ketosis, in a subject to which it is administered.

The term "mixed salt" or "multi-salt" is used herein to describe the portion of a ketogenic composition comprising a plurality of beta-hydroxybutyrate salts. The mixed salts include at least two, preferably at least three, more preferably at least four different cations that form multiple beta-hydroxybutyrate salts. In some embodiments, the salts can be proportioned to provide a balance set of electrolytes. In other embodiments, the salts can be proportioned to address a pre-existing electrolyte imbalance in a subject.

Ketosis" refers to a subject having blood ketone levels within the range of about 0.5 mmol/L and about 16 mmol/L. Ketosis may improve mitochondrial function, decrease reactive oxygen species production, reduce inflammation, and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

"Exogenous ketone body" refers to beta-hydroxybutyrate and acetoacetate compounds. These compounds may be utilized by a subject's body as an energy source during instances of low glucose levels or when these compounds are supplemented in a usable form. Where beta-hydroxybutyrate is included, it may be provided as purified or enriched with the R enantiomer, as purified or enriched with the S enantiomer, or as a racemic mixture. The exogenous ketone bodies may be provided in mixed salt form, optionally with an amount of the free acid of beta-hydroxybutyrate and/or acetoacetic acid, ester forms of these compounds, or combination thereof. Ketone body precursors such as 1,3-butanediol or ester thereof can be included.

Beta-hydroxybutyrate is the deprotonated form of beta-hydroxybutyric acid having the formula $CH_3CH_2OHCH_2COOH$. The deprotonated form present at typical biological pH levels is $CH_3CH_2OHCH_2COO^-$. The general chemical structure of beta-hydroxybutyrate is:

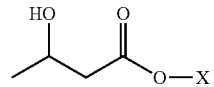

where, X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Acetoacetate is the deprotonated form of acetoacetic acid having the formula $CH_3COCH_2COOH$. The deprotonated form present at typical biological pH levels is $CH_3COCH_2COO^-$. The general chemical structure of acetoacetate is:

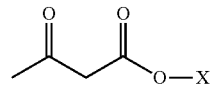

where, X can be hydrogen, metal ion, amino cation such as from an amino acid, alkyl, alkenyl, aryl, or acyl.

When X is a hydrogen, the compound is acetoacetic acid. When X is a metal ion or an amino cation, the compounds is an acetoacetate salt. When X is alkyl, alkenyl, aryl, or acyl, the compounds is an acetoacetate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

Example mixed salt compositions can include enantiomerically pure R-beta-hydroxybutyrate salts, enantiomerically pure S-beta-hydroxybutyrate salts, non-racemic mixtures enriched with R-beta-hydroxybutyrate salts relative to S-beta-hydroxybutyrate salts, non-racemic mixtures enriched with S-beta-hydroxybutyrate salts relative to R-beta-hydroxybutyrate salts, or a racemic mixture of RS-beta-hydroxybutyrate salts. Mixed salt compositions may include acetoacetate salts in combination with or in place of beta-hydroxybutyrate salts.

Whether beta-hydroxybutyrate is the R- or S-enantiomer depends on the tetrahedral orientation of the hydroxy (or oxy group in the case of an ester) on the 3-carbon (beta-carbon) in relationship to the planar carboxyl group. R-beta-hydroxybutyrate is the endogenous form of BHB and can be utilized by a patient's body as a fuel source during instances of low glucose levels in the subject or when a patient's body is supplemented with a usable form of beta-hydroxybutyrate. S-beta-hydroxybutyrate is not endogenously produced by mammals but can promote one or more of: increased endogenous production of R-beta-hydroxybutyrate and acetoacetate; endogenous conversion into one or both of R-beta-hydroxybutyrate and acetoacetate; endogenous conversion into fatty acids and sterols; prolonged ketosis; direct metabolism of S-beta-hydroxybutyrate; improved fetal development; increased growth years; reduced endogenous production of acetone during ketosis; signaling to modulate metabolism of R-beta-hydroxybutyrate and glucose; antioxidant activity; and production of acetyl-CoA.

The term "unit dose" refers to a dosage form that is configured to deliver a specified quantity or dose of mixed salt composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of mixed salt composition or component thereof is a unit dose measuring device, such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a mixed salt composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, syringes, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

The term "administration" or "administering" is used herein to describe the process in which the mixed salt compositions are delivered to a subject. The composition may be administered in various ways including oral, intragastric, and parenteral (referring to intravenous and intraarterial and other appropriate parenteral routes), among others.

In some embodiments, the mixed salt composition may be combined with a nutritionally or pharmaceutically acceptable carrier

II. Beta-hydroxybutyrate Mixed Salts

The administration of mixed beta-hydroxybutyrate salts results in elevated and sustained blood levels of ketone bodies, thereby exploiting the metabolic and physiological advantages of sustained ketosis, without introducing an excessive quantity of one electrolyte in the case of a mono salt. Raising the level of ketone bodies in the blood provides a subject with greater flexibility in diet options as compared to a method that aims to induce and sustain ketosis based on diet alone (e.g., based on fasting and/or limited carbohydrate intake). A subject that consumes an appropriate amount of mixed BHB salts will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

Subjects entering or maintaining a ketogenic state may already be in a state of electrolyte imbalance due to metabolic shifts involved with ketosis, including enhanced diuretic effects and changes in insulin profiles. Thus, while there are many benefits to the administration of BHB to promote or sustain ketosis in a subject, the resulting electrolyte imbalance and its associated detrimental physiological effects can offset the benefits of ketosis and/or make it more difficult for a subject to maintain ketosis at the desired levels or for a desired length of time.

Further, because BHB can be administered in salt form, where one or more BHB molecules are the anions to a selected cation, the introduction of additional cation electrolytes can exacerbate the electrolyte imbalance of the subject. For example, a formulation having an overly high level and/or an overly high proportion of a particular BHB salt can cause further electrolyte imbalance and/or cause other detrimental health effects. In some circumstances, even if the particular form of BHB salt eases an electrolyte imbalance to some degree, it can introduce other negative and undesirable health effects.

By way of example, a formulation having an overly high level and/or an overly high proportion of sodium BHB will increase the level of sodium in the subject. While sodium is a necessary nutrient, having levels that are outside of optimal ranges can lead to detrimental effects. High levels of sodium are associated with hypertension and poor cardiovascular health. In particular, high levels of sodium relative to potassium will promote hypertension and raise the risk of cardiovascular disease.

In another example, a formulation having an overly high level or an overly high proportion of calcium BHB will increase calcium levels in the subject. While calcium is also a necessary nutrient, and is particularly important for good bone health, excessive levels of calcium may not be fully absorbed into the bones and may instead build up in soft tissues, leading to detrimental calcification and hardening of the tissues and raising the risk of heart disease (e.g., associated with hardened arteries), kidney stones, arthritis, and other problematic conditions. In particular, high levels of calcium relative to magnesium can aggravate these negative effects. Magnesium functions by stimulating the hormone calcitonin and functions to convert vitamin D to its active form so it can promote calcium absorption in the bones as opposed to calcium deposition in soft tissues.

The administration of BHB salts in inappropriate amounts and proportions can therefore cause or aggravate detrimental health effects. Further, accounting for imbalances through other dietary options is not always easy or possible for a subject attempting to maintain a ketogenic state. For example, many of the foods known to have high levels of potassium and/or magnesium, such as whole grains, bananas, avocados, milk, yogurt, oatmeal, corn, peas, potatoes, and squash, contain high levels of carbohydrates and are incompatible with a strict ketogenic diet when consumed in any substantial amount.

Embodiments disclosed herein provide a therapeutically effective amount of beta-hydroxybutyrate in the form of a mixed BHB salt. Beneficially, the mixed BHB salt is formulated to provide a biologically balanced set of cation electrolytes. One or more embodiments therefore provide the advantages of initiating and/or sustaining ketosis while simultaneously promoting healthy electrolyte balance and effects. For example, embodiments disclosed herein are capable of promoting ketogenesis without aggravating negative electrolyte imbalances, without promoting other detrimental health effects associated with electrolyte imbalances, and in at least some circumstances, even improving or easing electrolyte imbalances.

In some embodiments, a BHB mixed salt contains at least two, preferably at least three, and more preferably at least four different cations, and the mixed salt is proportioned such that it provides an appropriate balance of electrolytes, such as 10-70% by weight of sodium BHB, 10-70% by weight of potassium BHB, 10-70% by weight of calcium BHB, and/or 10-70% by weight of magnesium BHB.

In some embodiments, sodium BHB salt is included in an amount ranging from about 5% to about 50%, or about 7.5% to about 40%, or about 10% to about 30%, or about 12% to about 25%, or about 14% to about 22%, or about 16% to about 20%, or about 18%, by weight of the mixed salt.

In some embodiments, potassium BHB salt is included in an amount ranging from about 5% to about 50%, or about 7.5% to about 40%, 10% to about 30%, or about 12% to about 25%, or about 14% to about 22%, or about 16% to about 20%, or about 18%, by weight of the mixed salt.

In some embodiments, calcium BHB salt is included in an amount ranging from about 5% to about 80%, or about 6% to about 60%, or about 7% to about 50%, or about 10% to about 40%, or about 12% to about 35%, or about 15% to about 30%, or about 18% to about 25%, or about 20% to about 23%, by weight of the mixed salt.

In some embodiments, magnesium BHB salt is included in an amount ranging from about 5% to about 80%, or about 6% to about 60%, or about 7% to about 50%, or about 10% to about 40%, or about 12% to about 35%, or about 15% to about 30%, or about 18% to about 25%, or about 20% to about 23%, by weight of the mixed salt.

In some embodiments, lithium BHB salt is included in an amount ranging from about 2% to about 30%, or about 3% to about 25%, or about 4% to about 20%, or about 5% to about 15, by weight of the mixed salt. Although high amounts of lithium salt can be harmful to the kidneys, small amounts of lithium can be tolerated and may improve mood and provide other health benefits.

In preferred embodiments, sodium BHB is included in an amount, by weight, no greater than the amount of potassium BHB, or no greater than two times the amount of potassium BHB. This advantageously enables administration of necessary sodium and potassium electrolytes, providing a beneficial electrolyte balance to the subject without causing or aggravating unwanted health effects associated with high sodium to potassium ratios (e.g., hypertension, cardiovascular disease, and other unfavorable effects).

In preferred embodiments, calcium BHB is included in an amount, by weight, no greater than the amount of magnesium BHB, or no greater than three times the amount of magnesium BHB, or no greater than two times the amount of magnesium BHB. This advantageously enables administration of necessary calcium and magnesium electrolytes, providing a beneficial electrolyte balance to the subject without causing or aggravating any of the unwanted health effects associated with high calcium to magnesium ratios (e.g., tissue calcification, poor bone health, and other unfavorable effects).

In preferred embodiments, mixed BHB salts can be formulated such that the molar ratio of sodium ions to potassium ions is no greater than 2:1, no greater than 1.5:1, or no greater than 1:1, and/or such that the molar ratio of calcium ions to magnesium ions in no greater than 3:1, no greater than 2:1, no greater than 1.5:1, or no greater than 1:1.

The mixed salt is preferably formulated so that an average daily dose of the ketogenic composition provides an amount of at least one of the cations of the mixed salt that is within a range of about 0.25 to about 10 times the recommended dietary allowance (RDA) of the of the at least one cation, or about 0.5 to 5 times, or about 0.75 to 2 times the RDA of the at least one cation. For example, the mixed salt may be formulated such that when a subject takes a daily amount of the mixed salt composition, the subject will have consumed an amount of the cation electrolyte falling within the foregoing ranges. In some embodiments, the mixed salt is formulated such that the at least one cation electrolyte falling within the foregoing ranges after a daily dose of the ketogenic compound is potassium and/or magnesium.

Of course, in some circumstances, RDA levels may be exceeded without necessarily experiencing toxicity or negative health effects. One of skill in the art will understand that in some circumstances, the mixed salt may be formulated such that one or more of the electrolytes is included in an amount that exceeds the RDA by more than 10 times the RDA, without necessarily causing detrimental effects, as long as the subject is able to excrete or otherwise handle the extra electrolyte load.

In some embodiments, mixed salt compositions may include one or more salts in which at least some of the cations are provided by one or more amino acids or other organic compounds that have a net positive charge at the pH at which the BHB salts are produced or provided. BHB-amino acid salts can provide soluble forms of BHB without providing electrolytes such as sodium, potassium, calcium or magnesium. This permits the manufacture of BHB salts with a reduced quantity of electrolytes and/or a more healthy amount and/or healthier balance of electrolytes, particularly where it is desired to delivered higher quantities of BHB for therapeutic reasons without further increasing electrolyte load. Suitable amino acids include amino acids that contain more than one amine group capable of being protonated to form a compound having a net positive charge, which can provide the counter cation for BHB anion. Examples include arginine, lysine, leucine, iso-leucine, histidine, ornithine, citrulline, glutamine, or other suitable amino acids or metabolites of amino acids (e.g., creatine). Some amino acids also provide health benefits. For example, arginine and citrulline can increase nitric oxide in the blood, which dilates blood vessels and improves blood circulation for persons with heart conditions (and may help men suffering from erectile dysfunction).

Some embodiments can include additional BHB salts as part of the mixed salt composition. For example, some embodiments may include one or more transition metal BHB salts. Transition metal cations suitable for use as part of the mixed BHB salt include zinc, iron, (e.g., as an iron II or iron III cation), chromium, manganese, cobalt, copper, molybdenum, and selenium.

In embodiments where a transition metal BHB salt is included, preferred salts include zinc BHB and iron BHB. Zinc BHB may be included in a range of about 2% to about 40%, or about 3% to about 30%, or about 4% to about 20%, or about 5% to about 15%, or about 7% to about 13%, by weight of the mixed salt. Iron BHB salt may be included in a range of about 2% to about 40%, or about 3% to about 30%, or about 4% to about 20%, or about 5% to about 15%, or about 7% to about 13%, by weight of the mixed salt.

In some embodiments, mixed salt compositions may be provided in solid or powder form as opposed to liquid or gel form. Such solid-form mixed salt compositions, in addition to promoting beneficial ketogenic effects and electrolytic effects described herein, can provide ease of manufacture and handling. For example, in a mixed salt formulation of various BHB salts, certain BHB salts will exhibit different material properties (e.g., hygroscopicity), and the relative amounts of the different salts in the mixed salt formulation will therefore affect the overall properties of the composition.

In some embodiments, mixed salt compositions may be provided as a liquid, such as in the form of a shot (ingested or injected), mouth spray, or drink for fast delivery and absorption. Liquid forms may include one or more liquid carriers, such as water, ethanol, glycerin, propylene glycol, 1,3-propandiol, and the like, into which the mixed BHB salts are dissolved or dispersed. The composition may include flavoring agents that help mask the taste of BHB salts. These include essential oils, such as peppermint, natural and artificial sweeteners, and other flavorants known in the art.

Manufacturing of the mixed salt formulations described herein has demonstrated that some BHB salts, such as potassium BHB and magnesium BHB, exhibit greater hygroscopicity than other BHB salts, such as sodium BHB and calcium BHB. Improperly proportioning BHB salts can create "sticky" formulations that do not flow or handle well, increasing manufacturing costs and potentially decreasing the shelf-life, stability, and efficacy of the mixed salt product.

Accordingly, mixed salt compositions are advantageously formulated and balanced to provide ketogenic and electrolyte benefits and advantages described herein, while not unduly or unacceptably resulting in material properties that overly hamper or disrupt manufacturability of the salt. In particular, at least some embodiments include different BHB salts in proportions that provide sufficient calcium BHB and/or sodium BHB (which typically promote manufacturability and handling) without including these salts at unduly high levels that would promote harmful health effects. Likewise, at least some embodiments include potassium BHB and/or magnesium BHB (which typically hamper manufacturability and handling) in amounts sufficient to balance the sodium and/or calcium BHB but not in excessive amounts that would unduly increase manufacturing difficulty.

III. Beta-Hydroxybutyrate Enantiomers

Beta-hydroxybutyrate salts can be provided in various enantiomeric forms, such as a racemic mixture of enantiomers, or RS-beta hydroxybutyrate (aka DL-beta hydroxybutyrate), which can be made synthetically. In humans, R-hydroxybutyrate (aka D-3-hydroxybutyrate, D-beta hydroxybutyrate, or "D-BHB") is synthesized in the liver from acetoacetate, the first ketone produced when fasting. Therefore, it may be desirable to provide BHB as R-hydroxybutyrate to increase potency, either enriched relative to S-hydroxybutyrate (aka L-3-hydroxybutyrate, L-beta hydrobutyrate, or "L-BHB") or isolated from S-hydroxybutyrate. Alternatively, it may be desirable to provide BHB as S-hydroxybutyrate, either enriched relative to R-hydroxybutyrate or isolated from R-hydroxybutyrate.

The percent enantiomer equivalents for each of R-beta-hydroxybutyrate and S-beta-hydroxybutyrate is defined by the molar quantity of either R-beta-hydroxybutyrate or S-beta-hydroxybutyrate divided by the total combined molar quantities of R-beta-hydroxybutyrate and S-beta-hydroxybutyrate. The amounts of any cations forming salts and/or alcohols forming esters are excluded and do not count in determining the percent enantiomeric equivalents for each of R-beta-hydroxybutyrate and S-beta-hydroxybutyrate.

In some embodiments, mixed salt compositions may comprise a non-racemic mixture that is enriched with R-beta-hydroxybutyrate compared to S-beta-hydroxybutyrate (i.e., that contains more than 50% and less than 100% by enantiomeric equivalents of R-beta-hydroxybutyrate and less than 50% and more than 0% by enantiomeric equivalents of S-beta-hydroxybutyrate). In some embodiments, a non-racemic mixture of R-beta-hydroxybutyrate and S-beta-hydroxybutyrate contains 50.1% to 99.9%, 50.2% to 99.8%, 50.3% to 99.7%, 50.4% to 99.6%, 50.5% to 99.5%, 51% to 99%, 52% to 98%, 53% to 97%, 54% to 96%, 55% to 95%, 57% to 93%, or 60% to 90% by enantiomeric equivalents of R-beta-hydroxybutyrate and 49.9% to 0.1%, 49.8% to 0.2%, 49.7% to 0.3%, 49.6% to 0.4%, 49.5% to 0.5%, 49% to 1%, 48% to 2%, 47% to 3%, 46% to 4%, 45% to 5%, 43% to 7%, 41% to 15%, or 40% to 10% by enantiomeric equivalents of S-beta-hydroxybutyrate.

In other embodiments, mixed salt compositions may comprise a non-racemic mixture that is enriched with S-beta-hydroxybutyrate compared to R-beta-hydroxybutyrate (i.e., that contains more than 50% and less than 100% by enantiomeric equivalents of S-beta-hydroxybutyrate and less than 50% and more than 0% by enantiomeric equivalents of R-beta-hydroxybutyrate). In some embodiments, a non-racemic mixture of S-beta-hydroxybutyrate and R-beta-hydroxybutyrate contains 50.1% to 99.9%, 50.2% to 99.8%, 50.3% to 99.7%, 50.4% to 99.6%, 50.5% to 99.5%, 51% to 99%, 52% to 98%, 53% to 97%, 54% to 96%, 55% to 95%, 57% to 93%, or 60% to 90% by enantiomeric equivalents of S-beta-hydroxybutyrate and 49.9% to 0.1%, 49.8% to 0.2%, 49.7% to 0.3%, 49.6% to 0.4%, 49.5% to 0.5%, 49% to 1%, 48% to 2%, 47% to 3%, 46% to 4%, 45% to 5%, 43% to 7%, 41% to 15%, or 40% to 10% by enantiomeric equivalents of R-beta-hydroxybutyrate.

In yet other embodiments, mixed salt compositions may comprise a racemic mixture that contains equal amounts of R-beta-hydroxybutyrate and S-beta-hydroxybutyrate. In some cases, a racemic mixture may include about 49.9% to about 50.1%, or about 49.92% to about 50.08%, or about 49.94% to about 50.06%, or about 49.96% to about 50.04%, or about 49.98% to about 50.02%, by enantiomeric equivalents of R-beta-hydroxybutyrate and about 50.1% to about 49.9%, or about 50.06% to about 49.94%, or about 50.04% to about 49.96%, or about 50.02% to about 49.98%, by enantiomeric equivalents of S-beta-hydroxybutyrate.

IV. Beta-Hydroxybutyrate Acids and Esters

R-beta-hydroxybutyrate and S-beta-hydroxybutyrate can be provided in other forms, such as acids and/or esters.

For example, mixed salt compositions can include mixed salt forms of beta-hydroxybutyrate in combination with the acid form. In some embodiments, the non-racemic mixture contains less than 100% of one or more beta-hydroxybutyrate salts and greater than 0% free beta-hydroxybutyric acid, such as up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 9'7%, and at least 75%, 80%, 85%, 90%, 92%, 94%, 95%, 96%, or 97%, by molar equivalents of one or more beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, by molar equivalents of free beta-hydroxybutyric acid.

In some embodiments, mixed salt compositions can include one or more beta-hydroxybutyrate esters, such as mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono- or di-ester of S-, R-, or S-R-1,3-butanediol, mono-, di-, or tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxy-carboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, and one or more polyacids, such as tartaric acid, citric acid, malic acid, succinic acid, and fumaric acid.

V. Other Components

Some embodiments also include one or more additional ketone body precursors or compounds, such as beta-hydroxybutyrate esters, beta-hydroxybutyrate oligomers, acetoacetate salts or esters, and/or other compounds that cause a rise in blood ketone levels without adding more electrolytes to the bloodstream.

In some embodiments, mixed salt compositions may include short-, medium-, and/or long-chain fatty acids and/or esters thereof.

Short chain fatty acids range contain 2 to 5 carbon atoms. Exemplary short chain fatty acids are acetic acid, propionic acid, butyric acid, isobutyric acid, valeric acid, and isovaleric acid. A short chain triglyceride (SCT) is a molecule having a glycerol backbone attached to three short chain fatty acids, although for purposes of this disclosure mono- and di-glycerides of short chain fatty acids are also included within the term "SCT" unless otherwise specified. An example SCT is tributyrin.

Medium chain fatty acids contain from 6 to 12 carbons. Exemplary medium chain fatty acids are caproic acid, caprylic acid, capric acid, and lauric acid. A medium chain triglyceride (MCT) is a molecule having a glycerol backbone attached to three medium chain fatty acids, although for purposes of this disclosure mono- and di-glycerides of medium chain fatty acids are also included within the term "MCT" unless otherwise specified. Medium chain fatty acids and mono-, di- and triglycerides thereof are ketone body precursors that can provide an additional source for the production of ketone bodies independent of beta-hydroxybutyrate. Compositions that contain a beta-hydroxybutyrate salt together with a medium chain fatty acid or ester thereof are disclosed in U.S. Pat. No. 9,138,420, which is incorporated by reference.

Long chain fatty acids contain more than 12 carbon atoms. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids. A long chain triglyceride (LCT) is a molecule having a glycerol backbone attached to three long chain fatty acids, although for purposes of this disclosure mono- and di-glycerides of long chain fatty acids are also included within the term "LCT" unless otherwise specified. Long chain fatty acids and mono-, di- and triglycerides thereof can be ketone body precursors that can provide an additional source for the production of ketone bodies independent of beta-hydroxybutyrate, although they are less easily converted to ketone bodies compared to medium chain fatty acids and MCTs.

Sources of medium chain fatty acid or ester thereof include coconut oil, coconut milk powder, fractionated coconut oil, palm oil, palm kernel oil, caprylic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

There is a practical limit to how much MCT or other fatty acid source can be ingested, with some individuals having lower tolerance for MCTs or other fatty acid sources (e.g., they may cause gastrointestinal issues). The ability of mixed BHB salts to provide a substantial increase in the amount of BHB delivered without providing excessive electrolyte loading, particularly excessive loading of certain electrolytes that are unhealthy in high doses, such as sodium and calcium ions, permits a person to sustain a high level of ketosis for a longer period of time without having to consume an excessive quantity of MCT or other fatty acid source. In other words, mixed BHB salt compositions may be substantially free of MCT or medium fatty acid (e.g., less than 10%, less than 8%, less than 6%, less than 5%, less than 4%, less than 3%, less than 2%, or less than 1%, by combined weight of BHB mixed salts and MCT or medium fatty acid) and still provide a desired quantity of ketone bodies to a subject.

Mixed salt compositions may include a therapeutically effective amount of vitamin $D_3$. Vitamin $D_3$ works in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 µg to about 200 µg, or about 10 µg to about 100 µg, or about 15 µg to about 75 µg of vitamin $D_3$.

Mixed salt compositions may include other vitamins and/or minerals as desired to provide desired nutritional or health benefits.

The mixed salt compositions may include a dietetically or pharmaceutically acceptable carrier. Examples include powders, liquids, tablets, capsules, food products, food additives, beverages, beverage additives, candies, suckers, pastilles, food supplements, sprays, injectables, and suppositories.

Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the otherwise poor taste of beta-hydroxybutyrate compounds. These include essential oils, such as peppermint, natural and artificial sweeteners, and other flavorants known in the art.

Mixed salt compositions may include one or more components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

VI. Administration

Mixed salt compositions can be used in a method for increasing ketone body level, including promoting and/or sustaining ketosis, in a subject comprising administering to a subject in need thereof a nutritionally or pharmaceutically effective amount of a mixed salt composition disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

Mixed salt compositions described herein may be administered to a subject in therapeutically effective dosages and/or in frequencies to induce or sustain ketosis. In some embodiments, a single dose may include an amount of BHB mixed salts ranging from about 1 to about 50 grams, or about 2 to about 40 grams, or about 5 to about 30 grams, or about 10 to about 20 grams. Mixed salt compositions may provide about 0.5 gram to about 25 grams, or about 0.75 gram to about 20 grams, or about 1 gram to about 15 grams, or about 1.5 grams to about 12 grams of beta-hydroxybutyrate, exclusive of the weight of the cations.

Mixed salt compositions can include or be administered together with other supplements, such as vitamin $D_3$, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

Mixed salt compositions may further include one or more short chain fatty acids, medium chain fatty acids, long chain fatty acids, fatty acid esters, or mono-, di- or triglycerides thereof in order to provide an additional source of ketone bodies for sustaining ketosis for a longer period of time compared to the beta-hydroxybutyrate mixed salts alone. In some embodiments, the composition may be administered such that the ratio of beta-hydroxybutyrate to short, medium, or long chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, ketogenic compositions can be administered via oral administration in solid and/or powdered form, such as in a powdered mixture (e.g., powder filled gelatin capsules), hard-pressed tablets, or other oral administration route known to those skilled in the art.

In some embodiments, multiple doses of the composition are administered over time. The frequency of administration of the composition can vary depending on any of a variety of factors, such as timing of treatment from previous treatments, objectives of the treatment, and the like. The duration of administration of the composition (e.g., the time period over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

VII. Examples

The following is a description of exemplary BHB mixed salt compositions and other ketogenic compositions useful for raising ketone levels in a subject, including inducing and/or sustaining a ketogenic state in a subject to which they are administered, while providing a balanced set of cationic electrolytes.

In some cases, the compositions can be a blend of beta-hydroxybutyrate salts, blend of beta-hydroxybutyrate salts and esters, blend of beta-hydroxybutyrate salts and free beta-hydroxybutyric acid(s), or blend of beta-hydroxybutyrate salts, beta-hydroxybutyrate esters, and free beta-hydroxybutyric acid(s), to provide a desired electrolyte balance, taste and/or pharmacokinetic response. The compositions can also be combined with short, medium, or long chain fatty acids, esters, glycerides, and other supplements as disclosed herein to provide a desired level of elevated ketone bodies and other effects.

Example 1

A beta-hydroxybutyrate mixed salt is prepared by mixing sodium BHB at 23% by weight, potassium BHB at 23% by weight, calcium BHB at 27% by weight, and magnesium BHB at 27% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 2

A beta-hydroxybutyrate mixed salt is prepared by mixing sodium BHB at 18% by weight, potassium BHB at 18% by weight, calcium BHB at 32% by weight, and magnesium BHB at 32% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 3

A beta-hydroxybutyrate mixed salt is prepared by mixing sodium BHB at 15% by weight, potassium BHB at 20% by weight, calcium BHB at 30% by weight, and magnesium BHB at 35% by weight. Vitamin $D_3$ is added in an amount of 800 IU for every 20 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray or liquid shot.

Example 4

A beta-hydroxybutyrate mixed salt is prepared by mixing sodium BHB at 15% by weight, potassium BHB at 15% by weight, calcium BHB at 35% by weight, and magnesium BHB at 35% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 5

A beta-hydroxybutyrate mixed salt is prepared by mixing sodium BHB at 30% by weight, potassium BHB at 30% by weight, calcium BHB at 20% by weight, and magnesium BHB at 20% by weight. Vitamin $D_3$ is added in an amount of 1200 IU for every 15 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray or liquid shot.

Example 6

A beta-hydroxybutyrate mixed salt is prepared by mixing sodium BHB at 15% by weight, potassium BHB at 15% by weight, calcium BHB at 18% by weight, magnesium BHB at 18% by weight, zinc BHB at 17% by weight, and iron BHB at 17% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 7

A beta-hydroxybutyrate mixed salt is prepared by mixing sodium BHB at 20% by weight, potassium BHB at 20% by weight, calcium BHB at 20% by weight, magnesium BHB at 20% by weight, and zinc BHB at 20% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 8

A beta-hydroxybutyrate mixed salt is prepared by mixing sodium BHB at 15% by weight, potassium BHB at 25% by weight, calcium BHB at 20% by weight, magnesium BHB at 25% by weight, and iron BHB at 15% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 9

A beta-hydroxybutyrate mixed salt is prepared by mixing sodium BHB at 15% by weight, potassium BHB at 15% by weight, calcium BHB at 20% by weight, magnesium BHB at 20% by weight, zinc BHB at 20% by weight, and iron BHB at 10% by weight. Vitamin $D_3$ is added in an amount of 600 IU for every 10 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray or liquid shot.

Example 10

A beta-hydroxybutyrate mixed salt is prepared by mixing sodium BHB at 23% by weight, potassium BHB at 23% by weight, calcium BHB at 27% by weight, and magnesium BHB at 27% by weight. The BHB mixed salt is readily administered as a ketogenic composition, such as in powder form as a dietary supplement mixed with food or drink, in the form of one or more capsules or tablets, or in liquid form such as a mouth spray or liquid shot.

Example 11

A beta-hydroxybutyrate mixed salt is prepared by mixing sodium BHB at 25% by weight, potassium BHB at 25% by weight, calcium BHB at 25% by weight, and magnesium BHB at 25% by weight. The BHB mixed salt is then mixed with an anti-caking agent, which is safe for human consumption, at a ratio of 4 to 1 to form a ketogenic composition readily administered to a subject, such as in powder form as a dietary supplement mixed with food or drink, or in the form of one or more capsules or tablets.

Example 12

Any of the foregoing beta-hydroxybutyrate mixed salts is combined with at least one medium chain fatty acid source selected from a medium chain triglyceride, medium chain fatty acid, monoglyceride of a medium chain fatty acid, diglyceride of a medium chain fatty acid, or triglyceride of a medium chain fatty acid having 6 to 12 carbons, or 8 to 10 carbons, to provide a ketogenic composition that provides prolonged ketosis over a greater period of time than would be provided by a given dosage of BHB mixed salt by itself. The ratio of medium chain fatty acid source to BHB salts is 4:1, 3:1, 2:1, 1:1 or 1:2.

Example 13

Any of the foregoing examples is modified by combining the mixed BHB salt with one or more short chain triglycerides and/or one or more short chain fatty acids and/or one or more mono- or diglycerides of short chain fatty acids.

Example 14

Any of the foregoing examples is modified by combining the mixed BHB salt with one or more long chain triglycerides and/or one or more long chain fatty acids and/or one or more mono- or diglycerides of long chain fatty acids.

Example 15

Any of the foregoing beta-hydroxybutyrate mixed salts includes one or more BHB salts of a cationic amino acid selected from arginine, lysine, leucine, iso-leucine, histidine, ornithine, citrulline, L-glutamine, or metabolite of an amino acid, such as creatine). The BHB-amino acid salt decreases the ratio of electrolytes to BHB anions in the composition.

Example 16

Any of the foregoing beta-hydroxybutyrate mixed salts is modified to include two, three, or more than four different types of BHB salts.

Example 17

Any of the foregoing beta-hydroxybutyrate mixed salts can include a non-racemic mixture of R-beta-hydroxybutyrate and S-beta-hydroxybutyrate, which is prepared by mixing one or more R-beta-hydroxybutyrate salts with a racemic mixture of R- and S-beta-hydroxybutyrate salts to provide greater than 50% and less than 100% by enantiomeric equivalents of R-beta-hydroxybutyrate salts and less than 50% and greater than 0% by enantiomeric equivalents of S-beta-hydroxybutyrate salts. Because the non-racemic mixture includes more of the R-beta-hydroxybutyrate enantiomer, the onset of ketosis is accelerated for a given dosage as compared to the same dosage of a racemic mixture. On the other hand, including the S-beta-hydroxybutyrate enantiomer provides for a longer state of ketosis and/or other benefits as disclosed herein compared to using pure R-beta-hydroxybutyrate salts.

Example 18

Any of the foregoing beta-hydroxybutyrate mixed salts can include a non-racemic mixture of S-beta-hydroxybutyrate and R-beta-hydroxybutyrate salts, which is prepared by mixing one or more S-beta-hydroxybutyrate salts with a racemic mixture of S- and R-beta-hydroxybutyrate salts to provide greater than 50% and less than 100% by enantiomeric equivalents of S-beta-hydroxybutyrate salts and less than 50% and greater than 0% by enantiomeric equivalents of R-beta-hydroxybutyrate salts. Because the non-racemic mixture includes more of the S-beta-hydroxybutyrate enantiomer, the onset of ketosis is delayed for a given dosage as compared to the same dosage of a racemic mixture.

Example 19

Any of the foregoing beta-hydroxybutyrate mixed salts can include a racemic mixture of R-beta-hydroxybutyrate and R-beta-hydroxybutyrate salts to provide 50% by enantiomeric equivalents of R-beta-hydroxybutyrate salts and 50% by enantiomeric equivalents of S-beta-hydroxybutyrate salts. Because the racemic mixture includes 50% by enantiomeric equivalents of R-beta-hydroxybutyrate mixed salts, the onset of ketosis is accelerated for a given dosage as compared to the same dosage enriched with S-beta-hydroxybutyrate salts. On the other hand, because the racemic mixture includes 50% by enantiomeric equivalents of S-beta-hydroxybutyrate mixed salts, the duration of sustained ketosis is increased for a given dosage as compared to the same dosage enriched with R-beta-hydroxybutyrate salts.

Example 20

Any of the foregoing beta-hydroxybutyrate mixed salts is modified by combining the mixed salt composition with one or more supplements, such as one or more vitamins, minerals, herbs, and others known in the art.

Example 21

Any of the foregoing beta-hydroxybutyrate mixed salts is modified by including free beta-hydroxybutyric acid, where the mixed salt composition contains less than 100% of hydroxybutyrate salts and greater than 0% of free beta-hydroxybutyric acid, including up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97% by molar equivalents of beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, by molar equivalents of free beta-hydroxybutyric acid.

Example 22

Any of the foregoing beta-hydroxybutyrate mixed salts is modified by including one or more esters of beta-hydroxybutyrate.

Example 23

Any of the foregoing beta-hydroxybutyrate mixed salts is modified by combining the mixed salt composition with one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof.

The resulting combined supplement is expected to provide greater lipolysis and/or fat oxidation effects than a similar dose utilizing a beta-hydroxybutyrate component enriched in R-beta-hydroxybutyrate or enriched in S-beta-hydroxybutyrate.

Example 24

Any of the foregoing beta-hydroxybutyrate mixed salts is modified by combining the mixed salt composition with one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng, Ginkgo biloba, Rhodiola rosea, Polygala tenuifolia, Muira puama, Eschscholzia californica, Convolvulus pluricaulis, Centella asiatica, Evolvulus alsinoides, Bacopa monnieri, Epimedium* herbs, *Ashwagandha* herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof.

The resulting combined supplement is expected to provide greater cognition, alertness, and/or mood effects than a similar dose utilizing a beta-hydroxybutyrate component enriched in R-beta-hydroxybutyrate or enriched in S-beta-hydroxybutyrate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A mixed salt composition for increasing blood ketone level in a subject, comprising:
   greater than 0% and up to 0.4% by molar equivalents of beta-hydroxybutyric acid; and
   at least 99.6% and less than 100% by molar equivalents of a plurality of beta-hydroxybutyrate salts selected from:
   sodium beta-hydroxybutyrate;
   potassium beta-hydroxybutyrate;
   calcium beta-hydroxybutyrate; and
   magnesium beta-hydroxybutyrate.

2. The mixed salt composition of claim 1, wherein the beta-hydroxybutyrate salts comprise enantiomerically pure R-beta-hydroxybutyrate salts or are enriched with R-beta-hydroxybutyrate salts so as to contain more than 50% by weight of the R-beta-hydroxybutyrate salts and less than 50% by weight of S-beta-hydroxybutyrate salts.

3. The mixed salt composition of claim 1, wherein the beta-hydroxybutyrate salts comprise enantiomerically pure S-beta-hydroxybutyrate salts or are enriched with S-beta-hydroxybutyrate salts so as to contain more than 50% by weight of the S-beta-hydroxybutyrate salts and less than 50% by weight of R-beta-hydroxybutyrate salts.

4. The mixed salt composition of claim 1, wherein the beta-hydroxybutyrate salts includes a racemic mixture of R- and S-beta-hydroxybutyrate salts so as to contain about 50% by weight of the R-beta-hydroxybutyrate salts and about 50% by weight of the S-beta-hydroxybutyrate salts.

5. The mixed salt composition of claim 1, wherein the beta-hydroxybutyrate salts comprise at least three of:
   sodium beta-hydroxybutyrate;
   potassium beta-hydroxybutyrate;
   calcium beta-hydroxybutyrate; and
   magnesium beta-hydroxybutyrate.

6. The mixed salt composition of claim 1, wherein the beta-hydroxybutyrate salts comprise:
   sodium beta-hydroxybutyrate;
   potassium beta-hydroxybutyrate;
   calcium beta-hydroxybutyrate; and
   magnesium beta-hydroxybutyrate.

7. The mixed salt composition of claim 6, wherein the sodium beta-hydroxybutyrate, the potassium beta-hydroxybutyrate, the calcium beta-hydroxybutyrate, and the magnesium beta-hydroxybutyrate are included in relative proportions so that a quantity of the composition that provides the recommended daily allowance (RDA) of calcium provides no more than the RDA for each of sodium, potassium, and magnesium.

8. The mixed salt composition of claim 1, wherein the molar ratio of sodium ions to potassium ions in the beta-hydroxybutyrate salts is no greater than 1.

9. The mixed salt composition of claim 1, wherein the amount of sodium beta-hydroxybutyrate salt, by weight, is no greater than the amount of potassium beta-hydroxybutyrate salt, by weight.

10. The mixed salt composition of claim 1, further comprising at least one short chain fatty acid having less than 6 carbons, or a mono-, di- or triglyceride of the at least one short chain fatty acid.

11. The mixed salt composition of claim 1, further comprising at least one supplement selected from vitamin, mineral, nootropic, and herbal supplement.

12. The mixed salt composition of claim 1, wherein the composition is substantially free of medium chain fatty acids or mono-, di-, or triglycerides thereof.

13. A liquid comprising a liquid carrier and the mixed salt composition of claim 1, wherein the liquid comprising is formulated for oral delivery.

14. A kit for administering ketone bodies to a subject, comprising:
the mixed salt composition of claim 1 in powder or solid form;
a container in which the mixed salt composition in powder or solid form is placed, wherein the container is selected from the group consisting of carton, box, can, jar, bag, pouch, bottle, jug, and keg; and
a measuring device configured to hold therein a unit dose, or fraction thereof, of the mixed salt composition in powder or solid form, wherein the measuring device is selected from the group consisting of cup, scoop, syringe, dropper, spatula, and spoon, and wherein a unit dose of the mixed salt composition contains about 0.5 g to about 25 g of beta-hydroxybutyrate mixed salts.

15. A mixed salt composition for increasing ketone level in a subject, comprising:
greater than 0% and up to 0.4% by molar equivalents of beta-hydroxybutyric acid; and
at least 99.6% and less than 100% by molar equivalents of a plurality of beta-hydroxybutyrate salts selected from:
sodium beta-hydroxybutyrate;
potassium beta-hydroxybutyrate;
calcium beta-hydroxybutyrate; and
magnesium beta-hydroxybutyrate;
wherein the composition is provided as or in a tablet, capsule, powder, food, food additive, drink, drink additive, or mouth spray.

16. The mixed salt composition of claim 15, wherein the beta-hydroxybutyrate salts comprise at least three of:
sodium beta-hydroxybutyrate;
potassium beta-hydroxybutyrate;
calcium beta-hydroxybutyrate; and
magnesium beta-hydroxybutyrate.

17. The mixed salt composition of claim 15, further comprising at least one supplement selected from vitamin, mineral, nootropic, and herbal supplement.

18. The mixed salt composition of claim 15, wherein the beta-hydroxybutyrate salts comprise enantiomerically pure R-beta-hydroxybutyrate salts or are enriched with R-beta-hydroxybutyrate salts so as to contain more than 50% by weight of the R-beta-hydroxybutyrate salts and less than 50% by weight of S-beta-hydroxybutyrate salts.

19. A mixed salt composition for increasing ketone level in a subject, comprising:
a liquid carrier;
greater than 0% and up to 0.4% by molar equivalents of beta-hydroxybutyric acid; and
at least 99.6% and less than 100% by molar equivalents of a plurality of beta-hydroxybutyrate salts selected from:
sodium beta-hydroxybutyrate;
potassium beta-hydroxybutyrate;
calcium beta-hydroxybutyrate; and
magnesium beta-hydroxybutyrate,
wherein the composition is substantially free of medium chain fatty acids or mono-, di-, or triglycerides thereof.

20. The mixed salt composition of claim 19, wherein the beta-hydroxybutyrate salts comprise at least three of:
sodium beta-hydroxybutyrate;
potassium beta-hydroxybutyrate;
calcium beta-hydroxybutyrate; or
magnesium beta-hydroxybutyrate.

21. The mixed salt composition of claim 19, further comprising at least one stimulant selected from the group consisting of caffeine, theobromine, theacrine, methylliberine, huperzine A, and epicatechins.

22. The mixed salt composition of claim 1, wherein the mixed salt composition comprises 0.1% 0.4% by molar equivalents of the beta-hydroxybutyric acid and 99.6% to 99.9% by molar equivalents of the plurality of beta-hydroxybutyrate salts.

23. The mixed salt composition of claim 15, wherein the mixed salt composition comprises 0.1% to 0.4% by molar equivalents of the beta-hydroxybutyric acid and 99.6% to 99.9% by molar equivalents of the plurality of beta-hydroxybutyrate salts.

24. The mixed salt composition of claim 19, wherein the mixed salt composition comprises 0.1% to 0.4% by molar equivalents of the beta-hydroxybutyric acid and 99.6% to 99.9% by molar equivalents of the plurality of beta-hydroxybutyrate salts.

* * * * *

UNITED STATES PATENT AND TRADEMARK OFFICE
CERTIFICATE OF CORRECTION

PATENT NO. : 10,973,786 B2
APPLICATION NO. : 16/996509
DATED : April 13, 2021
INVENTOR(S) : Gary Millet Page 1 of 1

It is certified that error appears in the above-identified patent and that said Letters Patent is hereby corrected as shown below:

On the Title Page

Page 2
Item (56), References Cited, Other Publications, change "Bastin et al., "Salt Slection and Optimisation Procedures for Pharmaceutical New Chemical Entities", American Chemical Society and The Royal Society of Chemistry, vol. 4, No. 5, 2000, pp. 427-435." to — Bastin et al., "Salt Selection and Optimisation Procedures for Pharmaceutical New Chemical Entities", American Chemical Society and The Royal Society of Chemistry, vol. 4, No. 5, 2000, pp. 427-435. —

Page 3
Item (56), References Cited, Other Publications, change "Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evalutation/15918." to — Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evalutation/15918. —

In the Specification

Column 1
Line 59, change "satisfy the its" to — satisfy its —

Column 10
Line 42, change "of the of the" to — of the —

Column 19
Line 60, change "creatine)." to — creatine. —

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*